United States Patent [19]

Kruger

[11] 4,303,390
[45] Dec. 1, 1981

[54] DENTAL ARTICULATOR

[75] Inventor: Bernard M. Kruger, West Caldwell, N.J.

[73] Assignee: Norbert Richter, New York, N.Y.; a part interest

[21] Appl. No.: 175,490

[22] Filed: Aug. 5, 1980

Related U.S. Application Data

[63] Continuation-in-part of Ser. No. 45,621, Jun. 5, 1979, abandoned.

[51] Int. Cl.³ .............................................. A61C 11/00
[52] U.S. Cl. ...................................................... 433/59
[58] Field of Search ...................................... 433/59, 56

[56] References Cited

U.S. PATENT DOCUMENTS

| | | | |
|---|---|---|---|
| 2,713,721 | 7/1955 | Page | 433/56 |
| 3,176,400 | 4/1965 | DePietro | 435/57 |
| 3,452,439 | 7/1969 | Lee | 433/56 |
| 3,478,431 | 11/1969 | DePietro | 433/57 |
| 3,590,487 | 7/1971 | Guichet | 433/62 |
| 3,593,424 | 7/1971 | Lee | 433/55 |
| 3,694,919 | 10/1972 | Lee et al. | 433/55 |
| 3,896,550 | 7/1975 | Lee | 433/56 |
| 3,908,271 | 9/1975 | Derda | 433/58 |
| 4,034,475 | 7/1977 | Lee | 433/56 |
| 4,047,302 | 9/1977 | Cheythey | 433/56 |
| 4,058,895 | 11/1977 | Mack et al. | 433/57 |
| 4,083,114 | 4/1978 | Acevedo | 433/55 |
| 4,128,942 | 12/1978 | Schleich | 433/60 |

*Primary Examiner*—Robert Peshock
*Attorney, Agent, or Firm*—Bernard Malina

[57] ABSTRACT

A dental articulator comprises an upper frame, a lower frame and a pair of condyle assemblies which permit articulating relative motion of the frames. The condyle assemblies each permit individual adjustment in an antero-posterior direction and a superior-inferior direction thus making possible the simulation study and correction of temporo-mandibular joint dysfunctions.

21 Claims, 7 Drawing Figures

DENTAL ARTICULATOR

This application is a continuation-in-part of my co-pending application Ser. No. 45,621 filed on June 5, 1979 and now abandoned.

BACKGROUND OF THE INVENTION

The present invention relates generally to the field of dental apparatus and more particularly to a novel dental articulator which is capable of precise adjustment in order to duplicate physiological dysfunctions of the temporo-mandibular joint.

The prior art related to dental apparatus includes a wide variety of dental articulator devices, each of which generally simulates the relationship of the upper and lower human jaws to each other and to the bones of the skull. In reconstructive or diagnostic dentistry, the dentist takes an impression of the patient's mouth, including the teeth and jaws and a plaster model thereof is then made in the dental laboratory before and during treatment. At the laboratory, the plaster model is mounted on a dental articulator which simulates the position of the upper and lower jaws and other bone structures to the skull to enable the dentist or laboratory technician to make the necessary diagnosis or reconstruction.

Dental researchers have recently become involved in the diagnosis and treatment of what is known as temporo-mandibular joint dysfunction. It has been learned that the movement of the mandible, or lower jaw, is subject to dysfunctional problems which could cause a wide variety of physical problems including migraine headaches, back pain, nervous tension and even hypoglycemia. These dysfunctional problems have been studied by means of transcranial X-rays which have resulted in knowledge concerning the displacements of the temporo-mandibular joint and even more important, a method by which these displacements can be accurately measured.

Although the quantitative knowledge regarding these displacements is available, it has not been possible to transfer these displacements to any of the presently available dental articulators and it has therefore not been possible to achieve accurate correction of these problems.

It is accordingly a major objective of the present invention to provide a dental articulator which permits the physiological displacements of the temporo-mandibular joint to be duplicated.

Another object of the present invention is to provide a dental articulator which facilitates the accurate incorporation of temporo-mandibular joint displacement information into the dental articulator.

Another object of the present invention is to provide a dental articulator which permits individual condyles to be adjusted independently with each condyle adjustable independently in an antero-posterior direction and in an inferior-superior direction.

Another object of the present invention is to provide a dental articulator which is capable of accurately maintaining temporo-mandibular joint displacements incorporated therein for an extended period of time to permit protracted corrective dental work.

Another object of the present invention is to provide a dental articulator which can provide accurate information regarding premature tooth contact.

Still another object of the present invention is to provide an adjustable dental articulator which is simple to operate and which comprises a relatively small number of simple parts which are economical of manufacture.

SUMMARY OF THE INVENTION

In accordance with the present invention there is provided a dental articulator which incorporates a pair of movable condylar assemblies, each of which is adjustable along an X, or horizontal axis and along a Y, or vertical axis. This permits the incorporation into the dental articulator, information regarding individual condyles which is displaced in an anterior or posterior direction, along the X axis or in a superior or inferior direction, along the Y axis.

The invention includes a pair of horizontal micrometer-type assemblies, each of which permits the calibrated movement of a condyle post assembly antero-posteriorly along the X axis. This adjustment provides for an altered maxillo-mandibular relationship from what is called a centric relation position, or a centric occlusion position. This centric occlusion position acts as a base line reference from which corrections can be made. These corrections give the dentist invaluable diagnostic information concerning premature tooth contacts as well as facilitating dental appliance construction. This antero-posterior adjustment capability is of great importance since it represents the first time that antero-posterior deviations of the condyles can be programmed into a dental articulator.

Each of the condyle post assemblies includes a calibrated threaded portion for adjustment of the assembly in a superior-inferior direction, along the Y axis, and four radially disposed index pins which project from the condyle post and which are located 90 degrees with respect to each other. The threaded portion is threaded through the horizontal micrometer-type assembly and is locked in place with a locknut. When the locknut is loosened, the condyle post may be rotated. Using the index pins as a gauge, each one-quarter turn of the condyle post results in an incremented height adjustment. When the desired height adjustment has been completed, the locknut is retightened to hold the condyle post securely in place.

This vertical adjustment permits an operator to easily and accurately move each of the condyle posts a known distance thereby permitting him to make an orthopedic correction for a superiorly displaced condyle.

In an alternative embodiment of the invention, the condyle posts are each mounted on a horizontal slide carriage which is capable of calibrated motion antero-posteriorly along the X axis. Each of the horizontal slide carriages are mounted on a vertical slide carriage which is capable of calibrated motion in a superior or inferior direction along the Y axis. Each of the slide carriages are actuated by a micrometer type lead screw and the motion of the slide carriages relative to the base of the dental articulator is measured by a pair of dial indicator type of motion transducers. A vertically oriented dial indicator transducer is mounted on the base and is in contact with the vertical slide carriage which moves along the Y axis and a horizontally oriented dial indicator is mounted on the vertical slide carriage and is in contact with the horizontal slide carriage which moves along the X axis. The X and Y displacements of each of the condyle posts can thus be adjusted and measured independently.

DETAILED DESCRIPTION OF THE INVENTION

Figure 1:
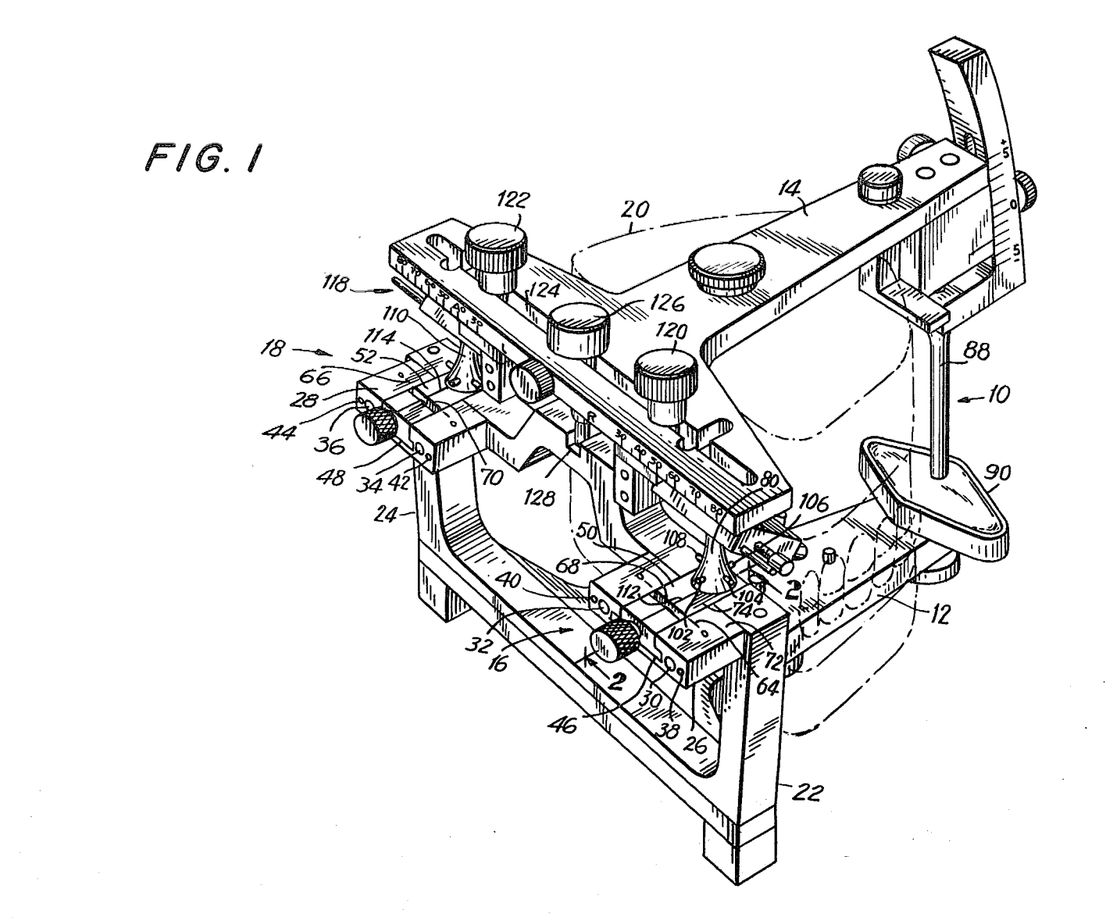
FIG. 1 is an overall perspective view of a dental articulator made in accordance with the present invention.

With reference to the drawings, there is shown in FIG. 1 a dental articulator 10 made in accordance with the present invention, comprising a base frame assembly 12 and an upper frame assembly 14 which respectively simulate the lower and the upper jaws of a human and a pair of adjustable condyle assemblies 16, 18 which form a major novel feature of the present invention.

The dental articulator 10, in a manner similar to conventional dental articulators, includes provisions for mounting models of upper and lower dentures, which are shown in phantom lines 20 in FIG. 1. The general function of the dental articulator 10 is to simulate the relative motion of the jaws of a patient to whom dentures are to be fitted or whose temporo-mandibular joint function is under study.

The base frame 12 includes a pair of upright members 22 and 24. A pair of guide blocks 26, 28 are fastened, one each, to the upright members 22, 24 by means of screws 30, 32, 34 and 36 and pins 38, 40, 42 and 44. The guide blocks 26, 28 have dovetail slots 46, 48 formed therein in which adjustable blocks 50, 52 are slidably mounted. The adjustable blocks 50, 52 are constrained by the dovetail slots 46, 48 to slide in straight line motion along the X axis as is defined in FIG. 2. It should be understood that details of construction of the adjustable condyle assembly 16, shown in FIG. 2, are also typical for the adjustable condyle assembly 18.

Figure 2:
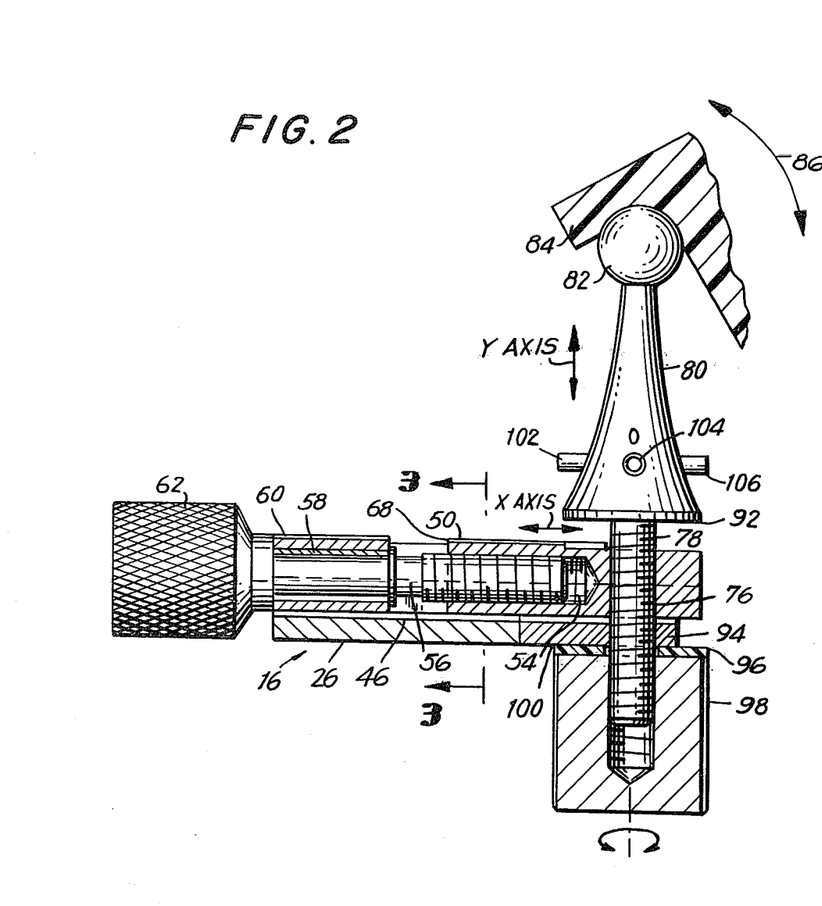
FIG. 2 is a fragmentary cross-sectional view taken along the line 2—2 of FIG. 1.
Figure 3:
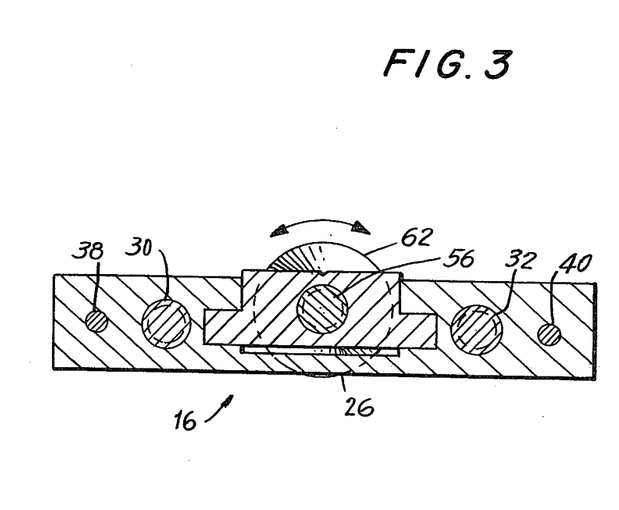
FIG. 3 is a fragmentary cross-sectional view taken along the line 3—3 of FIG. 2.

As is best shown in FIG. 2, the adjustable block 50 has an internally threaded portion 54 into which an accurate lead screw 56 is threaded. The lead screw 56 is rotatably mounted in a sleeve bearing 58 which is housed in a bearing block 60 which also fits in the dovetail slot 46. The lead screw 56 may be rotated by means of the knurled knob 62 resulting in translation of the adjustable block 50 with respect to the guide block 26. The guide blocks 26, 28 each have reference marks 64, 66 which, together with the edges 68, 70 of the adjustable blocks 50, 52 are used to gauge the position of the adjustable blocks 50, 52 along the X axis.

The lead screw 56 is in the nature of a precision micrometer lead screw having an accurate lead so that a single rotation of the knurled knobs 62, for example, results in a precisely calibrated motion of the adjustable block 50. Although not shown in the drawings, it is obvious that, as an alternative embodiment of the invention, in addition to the reference mark 64, the surface 72 of the guide block 26 may have engraved thereon, a millimeter scale. Additionally, in another alternative embodiment, the surface 74 of the adjustable block 50 may have engraved thereon, a vernier scale which may be used in conjunction with the millimeter scale to read displacements of the adjustable block 50 in the order of tenths of a millimeter.

The adjustable block 26 includes an internally threaded portion 76 which is located in line with the longitudinal axis of the lead screw 56 and is formed perpendicular to the lead screw 56. A threaded portion 78 of the condyle post 80 is threaded through the adjustable block 50. The upper end of the condyle post 80 includes a condyle 82 which cooperates with a maxillary articulation member 84 to facilitate articulation of the upper frame 14 of the dental articulator 10 in the direction indicated by the arrows 86 in FIG. 2. The front portion of the upper frame 14 is supported by an incisal rest pin 88, the lower surface of which engages the upper surface of a rest block 90, on the base frame 12.

The threaded portion 78 on the condyle post 80 is in the nature of a precision micrometer lead screw having an accurate lead similar to the lead screw 56. The condyle post 80 includes a shoulder portion 92 which, when seated on the upper surface of the adjustable block 50, provides a zero reference position for the vertical or Y axis motion of the condyle post 80.

The threaded portion 78 of the condyle post 80 is threaded through the adjustable block 50, passes through a slot 94 in the guide block 26, passes through a washer 96 and is threaded into a locknut 98. The washer 96, which may be made of teflon or a similarly suitable material, and the locknut 98 may be locked against the surface 100 of the guide block 26 thereby securely locking both the vertical and the horizontal position of the condyle post 80.

Four index pins 102, 104, 106 and 108 are provided, which project radially from an intermediate portion on each of the condyle posts 80, 110. The index pins 102, 104, 106 and 108 are disposed at 90 degrees to each other when viewed on a horizontal plane. When the locknut 98 is unlocked, and the condyle post 80 is rotated, the position of the index pins 102, 104, 106 and 108 with respect to the reference lines 112, 114 on the adjustable blocks 50, 52 gives a precise indication of the elevation of each of the condyle posts 80, 110 with respect to the adjustable blocks. This elevation represents motion along the Y axis as defined in FIG. 2. The condyle posts 80, 110 can thus be moved a known distance to orthopedically correct for a superiorly displaced condyle.

Adjustments of each of the two condyle posts 80, 110 in a superior or inferior direction, along the Y axis, may be made independently. In addition, as previously described, anterior or posterior adjustments of each of the two condyle posts 80, 110 along the X axis may be made independently. The X axis displacement of a condyle may be made completely independently of the Y axis displacement of the condyle. This feature enables an operator to simultaneously correct for posterior superior condyle displacements which cannot be accomplished on presently available instruments.

The maxillary articulation member 84 shown in FIG. 2 is part of a maxillary articular assembly 118 which includes setting screws 120, 122 for lateral adjustment within the slot 124. A centric setting screw 126 cooperates with a slot 128 to establish a laterally centric relationship between the base frame 12 and the upper frame 14. The centric setting screw 126 and the maxillary articulation assembly 118 are elements of conventional dental articulators and are therefore not described in detail.

In another alternative embodiment of the invention, which is not shown in the drawing, the condyle post passes through a hollow spindle on which there is an engraved mullimeter scale. The condyle post carries a circular thimble which encircles the spindle and which reveals more or less of the spindle as the condyle post moves down or up. The thimble has an engraved circular scale adjacent to its upper edge. The scales on the spindle and on the thimble correspond generally to the scales on the spindle and thimble of a conventional micrometer caliper and facilitate reading the vertical displacement of the condyle post in tenths of a millimeter.

Figure 4:
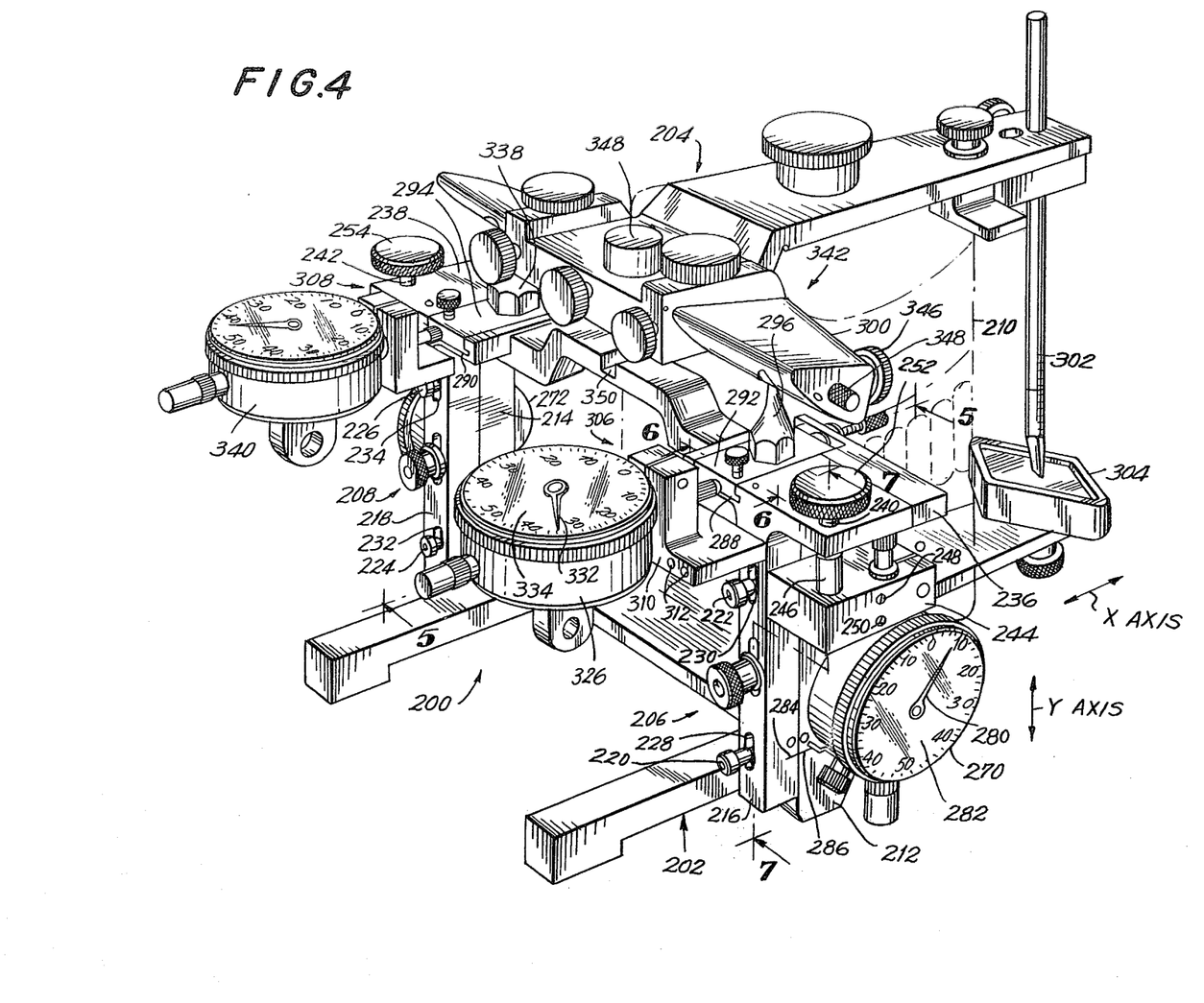
FIG. 4 is an overall perspective view of an alternative embodiment of the dental articulator according to the present invention.

Another alternative embodiment of a dental articulator according to the present invention is shown in FIG. 4 and is generally designated by the reference numeral 200. The dental articulator 200 comprises a base frame assembly 202, an upper frame assembly 204 and a pair of adjustable condyle assemblies 206, 208.

As has been previously described, the dental articulator 200 includes provisions, similar to conventional dental articulators, for mounting models 210 of upper and lower dentures, which are shown in phantom lines in FIG. 4.

Figure 7:
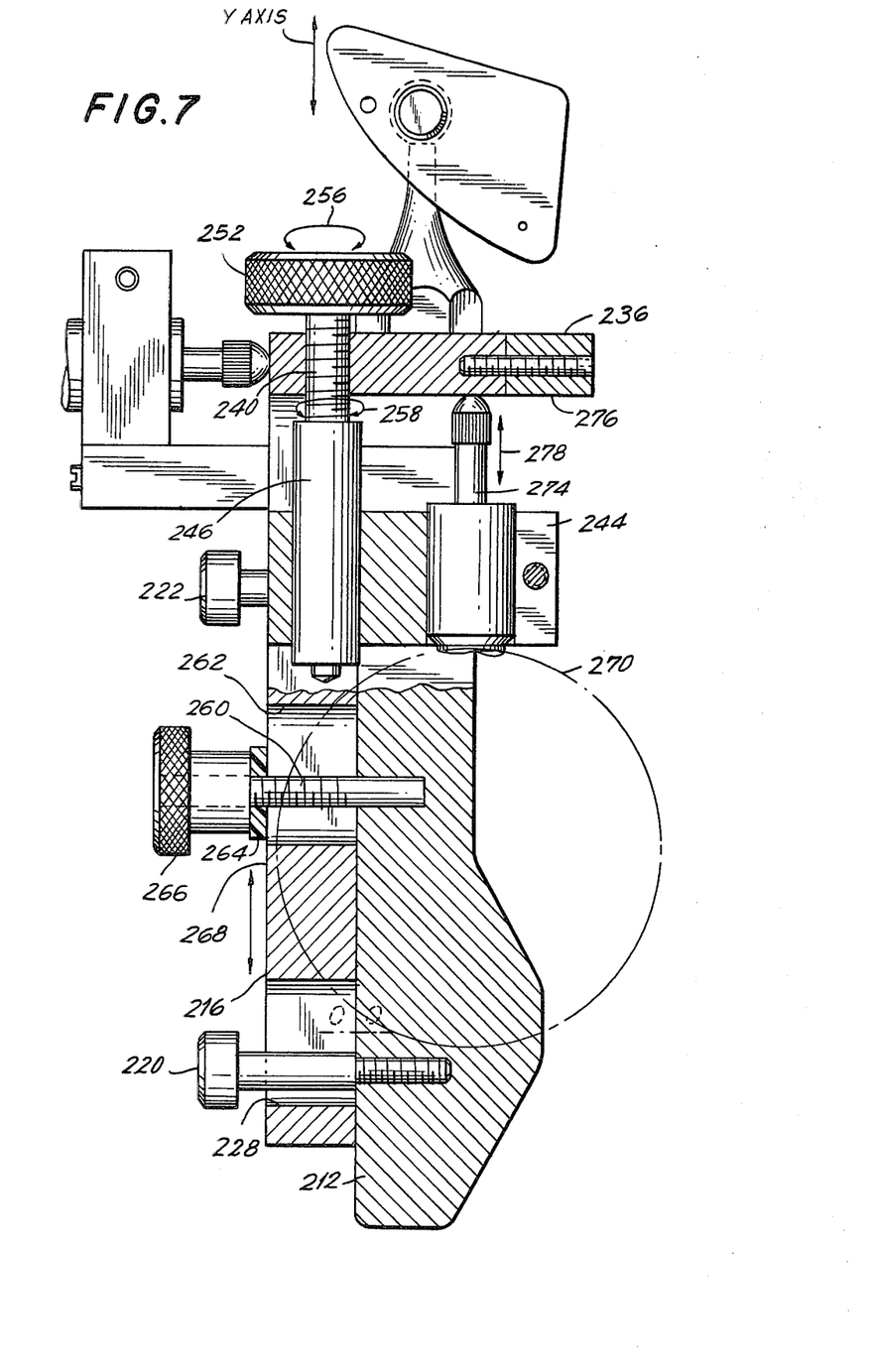
FIG. 7 is a fragmentary cross-sectional view taken along the line 7—7 of FIG. 4.

The base frame assembly 202 includes a pair of upright members 212, 214. The adjustable condyle assemblies 206, 208 include a pair of vertically oriented slide carriages 216, 218 which are mounted, one each, on the upright members 212, 214 by means of guide pins 220, 222, 224, 226 which project through the slots 228, 230, 232, 234 in the vertical slide carriages 216, 218. As is best shown in FIGS. 4 and 7, the vertical slide carriages 216, 218 each have a horizontal platform 236, 238 which is disposed at the upper ends of the vertical slide carriages. The horizontal platforms 236, 238 each include a vertically oriented lead screw 240, 242 which is threaded through the horizontal platform 236, 238, and which has a lower end which is rotatably attached to a horizontal shelf member 244, 246 via a sleeve member 246. The horizontal shelf member 244 is connected to the upright member 212 by means of screws 248 and 250. A similar horizontal shelf member, which is not shown, is similarly connected to the upright member 214.

The upper ends of the lead screws 240, 242 include adjustment knobs 252, 254 which, when rotated in the directions shown by the arrows 256 in FIG. 7, rotate the lead screws 240, 242 as shown by the arrows 258 and cause the vertical carriages 216, 218 to slide in straight line motion along the Y axis, as is defined in FIG. 7. The upright member 212 includes a threaded stud 260 which projects through a slot 262 formed in the slide carriage 216 and on which there is mounted a friction pad 264 and a knurled knob 266. Loosening the knurled knob 266 on the stud 260 permits the slide carriage 216 to slide along the upright member 212 as has been described. Tightening the knurled knob 266 causes the friction pad 264 to bear against the surface 268 of the slide carriage 216 and locks the slide carriage 216 in place. The relative distances between the horizontal shelf members 244 which are connected to the upright members 212, 214 of the base frame assembly 202 and the movable horizontal platforms 236, 238 are measured by a pair of dial indicators 270, 272 which are mounted on the horizontal shelf members 244 as is shown in FIG. 7. The upper end of the shaft 274 of the dial indicator 270 bears against the lower surface 276 of the horizontal platform 236 and the motion of the horizontal platform 236 in the direction shown by the arrows is sensed by the dial indicator 270 and is displayed by the needle 280 on the dial 282.

The upright members 212, 214 and the slide carriages 216, 218 each have a zero reference mark 284, 286 engraved thereon, which establishes a reference for inferior and superior motion along the Y axis. It should be understood that the details of construction of the vertical carriage 216 are also typical of the vertical carriage assembly 218.

The upper portions of the horizontal platforms 236, 238 each include a dovetail slot 288, 290 formed therein, in which adjustable guide blocks 292, 294 are slidably mounted. The adjustable guide blocks 292, 294 are constrained by the dovetail slots 288, 290 to slide in straight line motion along the X axis as is defined in FIGS. 2 and 5.

A condyle post 296 is mounted on the upper surface of the guide blocks 292, 294 by means of a threaded portion 298. The upper end of the condyle post 296 includes a condyle 298 which cooperates with a maxillary articulation member 300 to facilitate articulation of the upper frame assembly 204 of the dental articulator 200 in a manner similar to that which has been previously described. The front portion of the upper frame assembly 202 is supported by an incisal rest pin 302, the lower surface of which engages the upper surface of a rest block 304 on the base frame assembly 202.

Figures 5, 6:
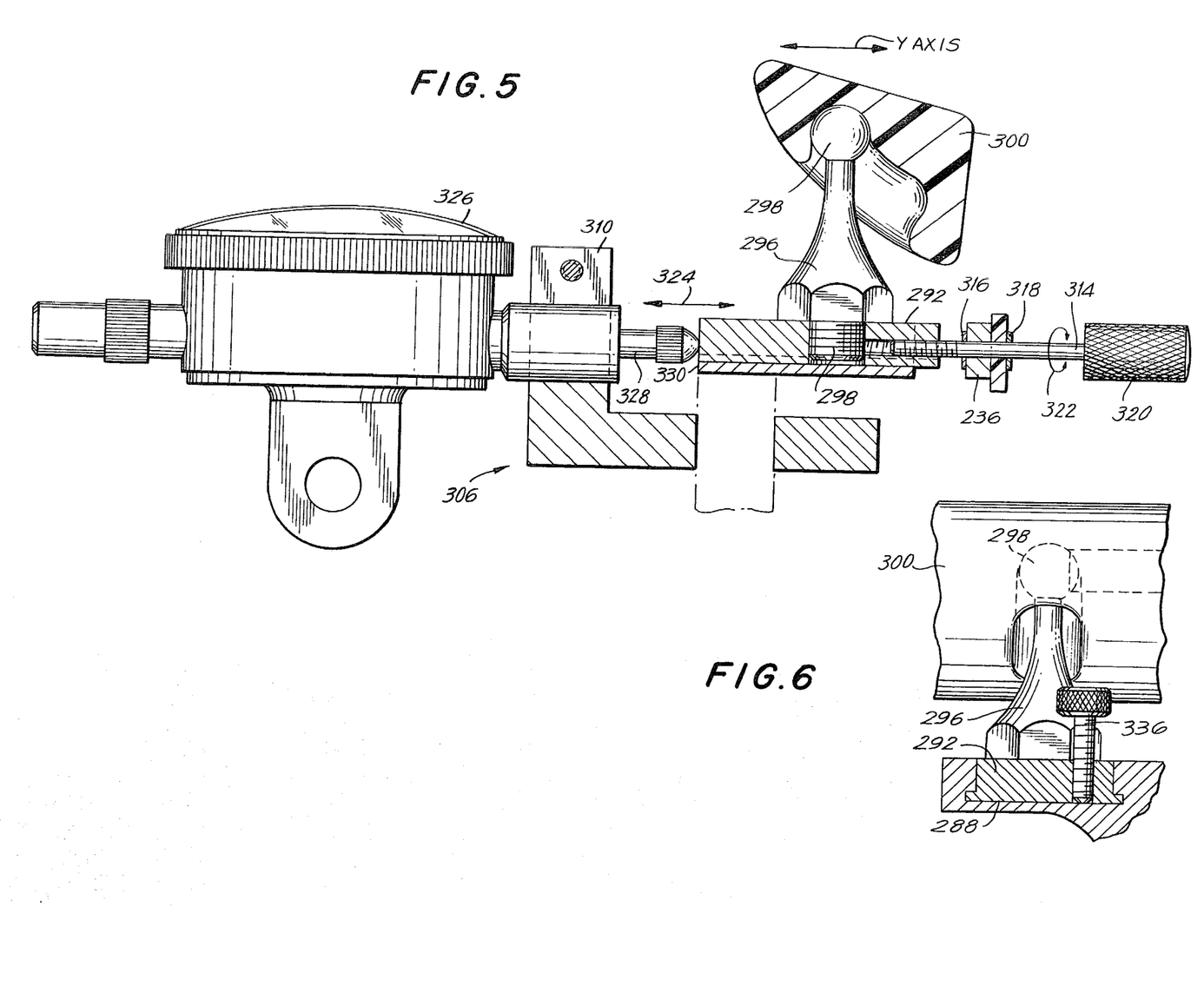
FIG. 5 is a fragmentary cross-sectional view taken along the line 5—5 of FIG. 4.
FIG. 6 is a fragmentary cross-sectional view taken along the line 6—6 of FIG. 4.

The upper portion of the horizontal platform 236 and the guide block 292 form part of a horizontal carriage assembly 306, the construction of which is also typical of the horizontal carriage assembly 308. The horizontal carriage assembly 308 includes a support block 310 which is mounted on the vertical slide carriage 216 by means of pins 312 and a horizontally oriented lead screw 314. As is best shown in FIGS. 4 and 5, the horizontal lead screw 314 passes through a projecting portion of the horizontal platform 236 and is threaded into the guide block 292. The axial position of the horizontal lead screw 314 with respect to the horizontal platform 236 is maintained by washers 316 and 318 which are mounted on the lead screw 314.

The horizontal lead screw 314 includes a knurled knob 320 which, when rotated in the direction shown by the arrows 322 in FIG. 5, causes the guide block 292 to translate in the direction shown by the arrows 324. The motion of the guide block 292 is sensed by a horizontally disposed dial indicator 326, which is mounted on the support block 310. The shaft 328 of the dial indicator 326 bears against the surface 330 of the guide block 292 and the motion of the guide block 329 is displayed by the needle 332 on the dial 334.

The guide block 292 may be locked in place by means of a set screw 336 which is threaded through the guide block 292 and which bears against the bottom surface of the dovetail slot 288.

It should be understood that the details of construction of the horizontal carriage assembly 306 which have been described are also typical of the horizontal carriage assembly 308.

Adjustments of each of the two condyle posts 296, 338 in a superior or inferior direction along the Y axis may be made independently and the amount of vertical adjustment of the condyle posts 296, 338 may be read directly on the dial indicators 270, 272. In addition, anterior or posterior adjustments of each of the two condyle posts 296, 338 along the X axis may be made independently and the amount of horizontal adjustment may be read directly on the dial indicators 326, 340. The X axis displacement of a condyle may be made completely independently of the Y axis displacement of the condyle.

The maxillary articulation member 300 shown in FIG. 4 is part of a maxillary articulation assembly 342 which includes setting screws 344, 346 for rotary adjustment of the maxillary articulation member. A centric setting screw 348 cooperates with a slot 350 to establish a laterally centric relationship between the base frame 202 and the upper frame 204. The centric setting screw 348 and the articulation assembly 342 are elements of conventional dental articulators and are therefore not described in detail.

Additional embodiments of the invention may include alternate means for measuring the horizontal and vertical displacements of the condyle posts. These means may include electrical means such as linear variable differential transformer devices with electrical readout instrumentation.

While preferred embodiments of the invention have been shown and described herein it is obvious that numerous omissions, changes and additions may be made in such embodiments without departing from the spirit and scope of the invention.

What is claimed is:

1. A dental articulator comprising a base frame, an upper frame, a pair of adjustable condyle means, mounted on said base frame and supporting said upper frame for pivotal motion of said upper frame relative to said base frame, with each of said adjustable condyle means comprising a condyle post, condyle post supporting means for independent horizontal adjustment of said condyle post relative to said base frame, and vertical adjustment means for vertical adjustment of said condyle post relative to said base frame.

2. A dental articulator according to claim 1, in which said vertical adjustment means is mounted on said horizontal adjustment means.

3. A dental articulator according to claim 1, in which said horizontal adjustment means comprises a support member mounted on said base frame, with said support member having a horizontally disposed guide way, a slide member slidably mounted in said guide way, with said condyle post mounted on said slide member and with said slide member having an internally threaded portion disposed parallel to said guide way, and a threaded shaft, threaded partially into said slide member, with rotation of said shaft moving said slide member and said condyle post in a horizontal direction.

4. A dental articulator according to claim 3 in which said slide member further includes a vertically disposed threaded portion, and in which said condyle post includes a threaded portion fitting said vertically disposed threaded portion on said slide member, so that rotation of said condyle post with respect to said slide member results in a vertical displacement of said condyle post with respect to said base frame.

5. A dental articulator according to claim 4, in which said threaded portion of said condyle post passes through said slide member, and through said support member and further including a locknut which is threaded onto said threaded portion of said condyle post.

6. A dental articulator according to claim 4 in which said condyle posts each include a plurality of radially disposed projecting pins and in which said slide member includes a reference mark for indexing the rotation of said pins and thereby quantitatively determining the vertical displacement of said condyle post.

7. A dental articulator according to claim 6, in which said plurality of projecting pins comprises four pins orthogonally disposed relative to each other on a horizontal plane.

8. A dental articulator according to claim 4, further comprising a washer mounted on said threaded portion of said condyle post between said locknut and said support member.

9. A dental articulator according to claim 1, further comprising horizontal measurement means for measuring horizontal displacement of said condyle post and vertical measurement means for measuring vertical displacement of said condyle post.

10. A dental articulator according to claim 3, comprising a base scale mounted on said support member adjacent to said slide member and a vernier scale mounted on said slide member cooperating with said base scale for accurate measurement of relative motion between said slide member and said support member.

11. A dental articulator according to claim 3, further comprising a micrometer spindle scale encircling a portion of said condyle post and micrometer thimble means, having a circular scale with said micrometer thimble means carried by said condyle post and encircling said spindle scale to enable said spindle scale in cooperation with said circular scale on said micrometer thimble means to accurately measure vertical displacements of said condyle post.

12. A dental articulator according to claim 1, in which said horizontal adjustment means is mounted on said vertical adjustment means.

13. A dental articulator according to claim 1 in which each of said adjustable condyle means comprises an upright member mounted on said base frame and projecting vertically upward from said base frame, a vertical slide member slideably mounted on said upright member, with said vertical slide member having a horizontally disposed guide way, a horizontal slide member slideably mounted in said guide way and with said condyle post mounted on said horizontal slide member.

14. A dental articulator according to claim 13 further comprising locking means for reversibly locking said horizontal slide member to said vertical slide member.

15. A dental articulator according to claim 13 further comprising locking means for reversibly locking said vertical slide member to said upright member.

16. A dental articulator according to claim 13 further comprising a vertically disposed lead screw threaded through said vertical slide member and rotationally connected to said base frame, so that rotation of said vertically disposed lead screw causes a vertical displacement of said vertical slide member relative to said base frame.

17. A dental articulator according to claim 13 further comprising a horizontally disposed lead screw rotationally mounted on a portion of said vertical slide member and threaded into said horizontal slide member so that rotation of said horizontally disposed lead screw causes a horizontal displacement of said horizontal slide member relative to said vertical slide member.

18. A dental articulator according to claim 13, further comprising horizontal displacement measurement means for measuring horizontal displacement of said condyle post.

19. A dental articulator according to claim 13 further comprising vertical displacement measurement means for measuring vertical displacement of said condyle post.

20. A dental articulator according to claim 18 in which said horizontal displacement measurement means comprises horizontally disposed dial indicator displacement gauge means, mounted on said vertical slide member and disposed for measurement of displacement of said horizontal slide member relative to said vertical slide member.

21. A dental articulator according to claim 19 in which said vertical displacement measurement means comprises vertically disposed dial indicator displacement gauge means, mounted on said upright member and disposed for measurement of displacement of said vertical slide member relative to said base frame.

* * * * *